(12) United States Patent
Al-Jazaeri

(10) Patent No.: US 9,517,185 B1
(45) Date of Patent: Dec. 13, 2016

(54) FEEDING TUBE SYSTEM

(71) Applicant: KING SAUD UNIVERSITY, Riyadh (SA)

(72) Inventor: Ayman Al-Jazaeri, Riyadh (SA)

(*) Notice: Subject to any disclaimer, the term of this patent is extended or adjusted under 35 U.S.C. 154(b) by 0 days.

(21) Appl. No.: 14/886,423

(22) Filed: Oct. 19, 2015

(51) Int. Cl.
*A61M 15/00* (2006.01)
*A61J 15/00* (2006.01)
*A61M 39/02* (2006.01)

(52) U.S. Cl.
CPC ......... *A61J 15/0053* (2013.01); *A61J 15/0015* (2013.01); *A61J 15/0042* (2013.01); *A61J 15/0049* (2013.01); *A61M 2039/0255* (2013.01); *A61M 2039/0261* (2013.01); *A61M 2210/1042* (2013.01)

(58) Field of Classification Search
CPC .. A61J 15/0015; A61J 15/0026; A61J 15/003; A61J 15/0034; A61J 15/0038; A61J 15/0042; A61J 15/0046; A61J 15/0049; A61J 15/0053; A61J 15/0057; A61J 15/0061; A61J 15/0065; A61J 15/0096; A61M 2039/055; A61M 2039/0261; A61M 2039/027; A61M 2039/0273; A61M 2039/0276; A61M 2039/0279; A61M 2039/0282; A61M 2039/0297
See application file for complete search history.

(56) References Cited

U.S. PATENT DOCUMENTS

| | | | |
|---|---|---|---|
| 3,915,171 A | 10/1975 | Shermeta | |
| 4,666,433 A | 5/1987 | Parks | |
| 4,699,616 A | 10/1987 | Nowak et al. | |
| 4,798,592 A | 1/1989 | Parks | |
| 5,910,128 A | 6/1999 | Quinn | |
| 6,997,909 B2 | 2/2006 | Goldberg | |
| 7,819,840 B2 | 10/2010 | Burnside et al. | |
| 8,562,560 B2 | 10/2013 | Adams et al. | |
| 2007/0239108 A1* | 10/2007 | Albrecht | A61B 17/3415 604/96.01 |
| 2008/0097491 A1* | 4/2008 | Gobel | A61B 17/0644 606/153 |
| 2010/0081991 A1* | 4/2010 | Swisher | A61J 15/0042 604/101.05 |
| 2012/0180787 A1* | 7/2012 | Bosel | A61M 16/0472 128/200.26 |
| 2013/0165862 A1 | 6/2013 | Griffith et al. | |

* cited by examiner

Primary Examiner — Imani Hayman
Assistant Examiner — James D Ponton
(74) Attorney, Agent, or Firm — Richard C. Litman

(57) ABSTRACT

The feeding tube system includes an elongated shaft having a proximal portion, an opposing distal portion, and a central opening or lumen extending therethrough. The proximal portion is configured to remain outside a patient's body cavity and includes a first opening through which fluids can be introduced into the lumen. The distal portion is configured for disposing within a patient's body cavity and includes a second opening for discharging fluids from the lumen into the patient's body cavity. An interior retention balloon is provided at the distal portion of the elongated shaft. An external base positioned at the proximal portion of the feeding tube can include at least one exterior base balloon extending therefrom. The interior retention balloon and the at least one exterior base balloon are inflatable.

2 Claims, 5 Drawing Sheets

FEEDING TUBE SYSTEM

BACKGROUND OF THE INVENTION

1. Field of the Invention

The present invention relates to medical devices, and particularly to a feeding tube having a base balloon system.

2. Description of the Related Art

Percutaneous tubes, such as feeding tubes, are normally used to administer fluids to patients through their body cavities, such as directly into their stomach or their intestine. Such feeding tubes are typically inserted into a patient's intestine or stomach through an opening in the patient's abdominal wall. With conventional feeding systems, however, it is often difficult to provide a constant seal between the tube and the opening of the patient's intestine or stomach through which the tube extends. Such a seal is important to prevent leakage through the opening.

Thus, a feeding tube system solving the aforementioned problems is desired.

SUMMARY OF THE INVENTION

The feeding tube system includes an elongated shaft having a proximal portion, an opposing distal portion, and a central opening or lumen extending therethrough. The proximal portion is configured to remain outside a patient's body cavity and includes a first opening through which fluids, such as medication and nutrients, can be introduced into the shaft. The distal portion is configured for positioning within a patient's body cavity and includes a soft tip having a second opening for discharging fluids from the lumen into the patient's body cavity. An interior retention balloon is provided at the distal portion of the elongated shaft. An external base positioned at the proximal portion of the feeding tube can include at least one exterior base balloon extending therefrom. The interior retention balloon is inflatable to properly position the elongated shaft inside the patient's body cavity and seal any space or gap between the shaft and the opening of the patient's body cavity through which the tube extends. The at least one exterior base balloon is also inflatable to lift and further stabilize the elongated shaft.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
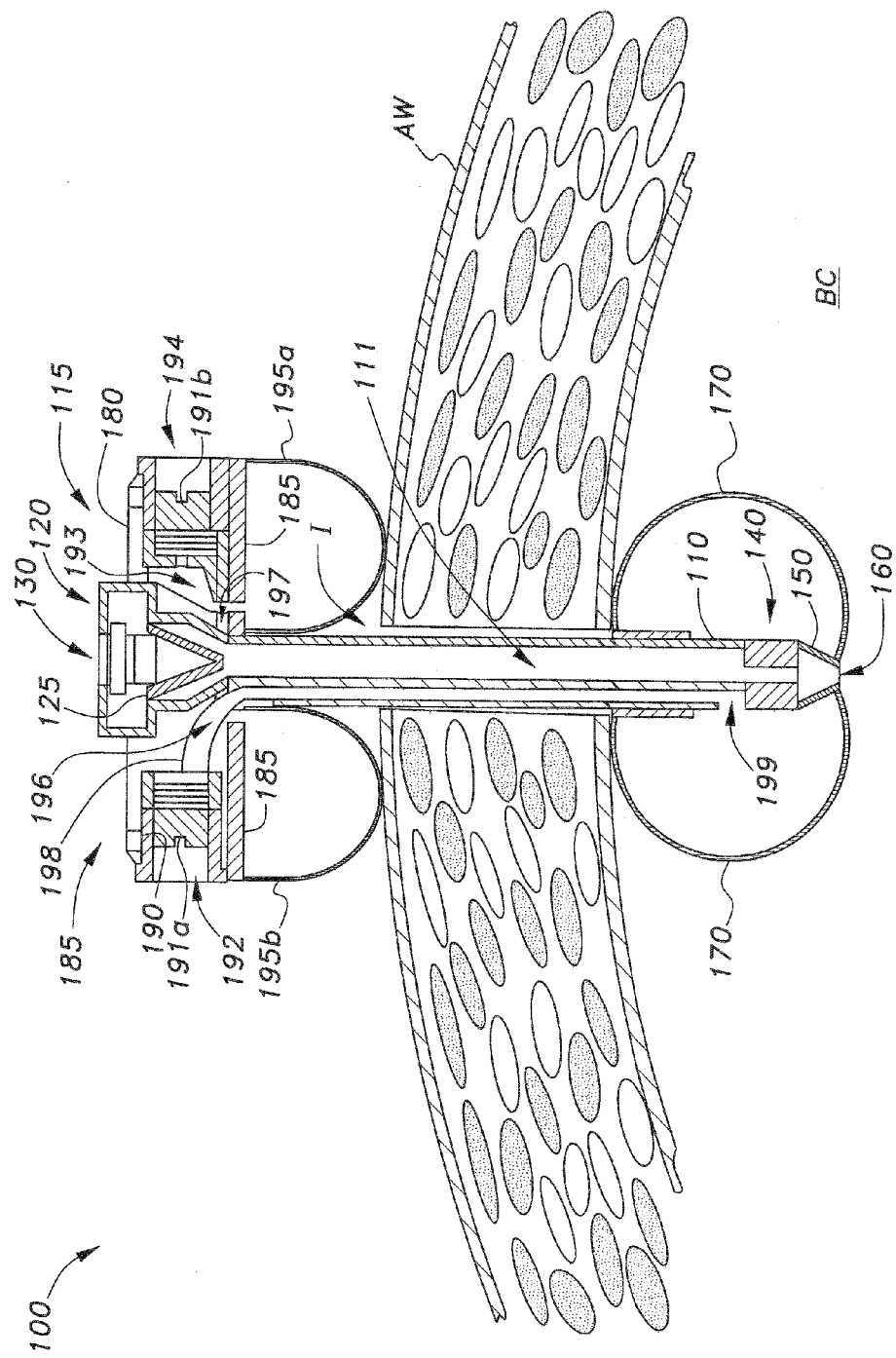
FIG. 1 is an environmental, a cross sectional view of a feeding tube connected to a body cavity, according to the present invention.

Referring to FIGS. 1 through 5, a feeding tube system 100, is generally illustrated. The feeding tube system 100 can include an elongated shaft 110 having a proximal portion 120, an opposing distal portion 140, and a central opening or lumen 111 extending therethrough. An interior retention balloon 170 is provided at the distal portion 140 of the elongated shaft 110. An external base 115 is provided at the proximal portion 120 of the elongated shaft 110. The external base 115 has an upper horizontal support 180 and a lower horizontal support 185, which extend normal to the shaft 110. A first exterior base balloon 195a can extend from a first portion of the lower horizontal support 185 of the external base 115. It is to be noted that a second external base balloon 195b can extend from a second portion of the lower horizontal support 185 of the external base 115. The proximal portion 120 includes a first opening 130 for receiving fluids, such as medication and nutrients. The distal portion 140 includes a soft tip 150 having an output port or second opening 160 for discharging fluids from the lumen 111 into a patient's body cavity BC, such as the stomach or intestine. As will be discussed in detail below, the interior retention balloon 170 is inflatable to properly position the elongated shaft 110 inside the patient's body cavity BC and close up the space between the shaft 110 and the opening of the patient's body cavity BC through which the tube extends. The first exterior base balloon 195a is also inflatable to lift and further stabilize the elongated shaft 110.

A first inflation port 192 is provided between upper horizontal support 180 and lower horizontal support 185. The first inflation port 192 is in communication with the internal retention balloon 170 through a first air channel 196. The first air channel 196 has an upper end 198 and a lower end 199. The first inflation port 192 provides an opening through which air may enter the system 100 for inflating the interior retention balloon 170 through the lower end 199. A second inflation port 194 is provided between upper horizontal support 180 and lower horizontal support 185. The second inflation port 194 is in communication with the first exterior base balloon 195a through a second air channel 193. The second inflation port 194 provides an opening through which air may enter the system 100 for inflating the first exterior base balloon 195a. Accordingly, air from an air source, such as a pump (not shown), can be pumped into the first inflation port 192 and through the first air channel 196 to inflate the internal retention balloon 170. Similarly, air can be pumped into the second inflation port 194, and through the second air channel 193 into the first exterior base balloon 195a. A side channel 197 can be defined within the lower horizontal support 185 to permit air to pass from the second air channel 193 into the second external base balloon 195b.

Figure 3:
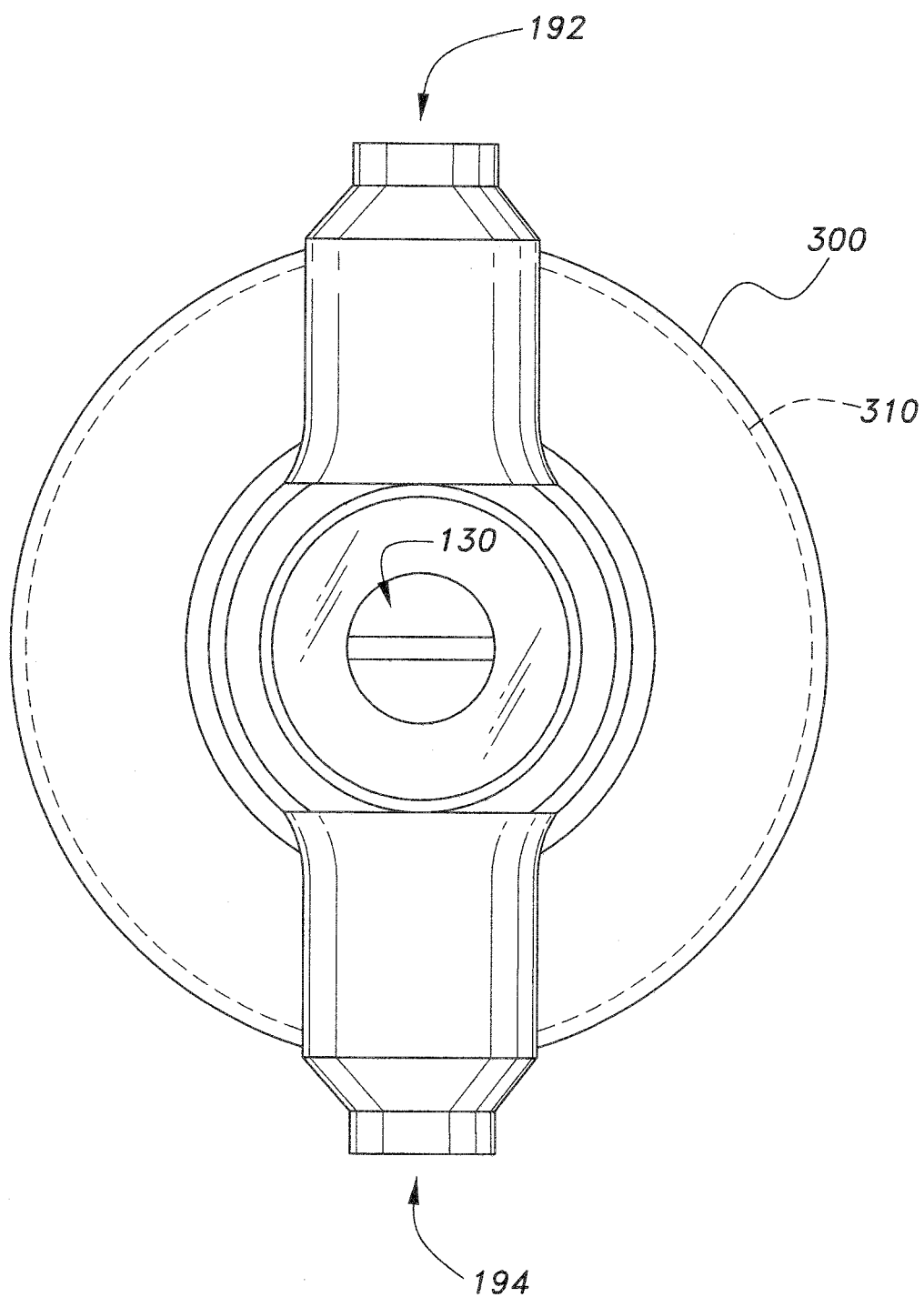
FIG. 3 is a top plan view of a feeding tube system including a circular base plate, according to the present invention.
Figure 4:
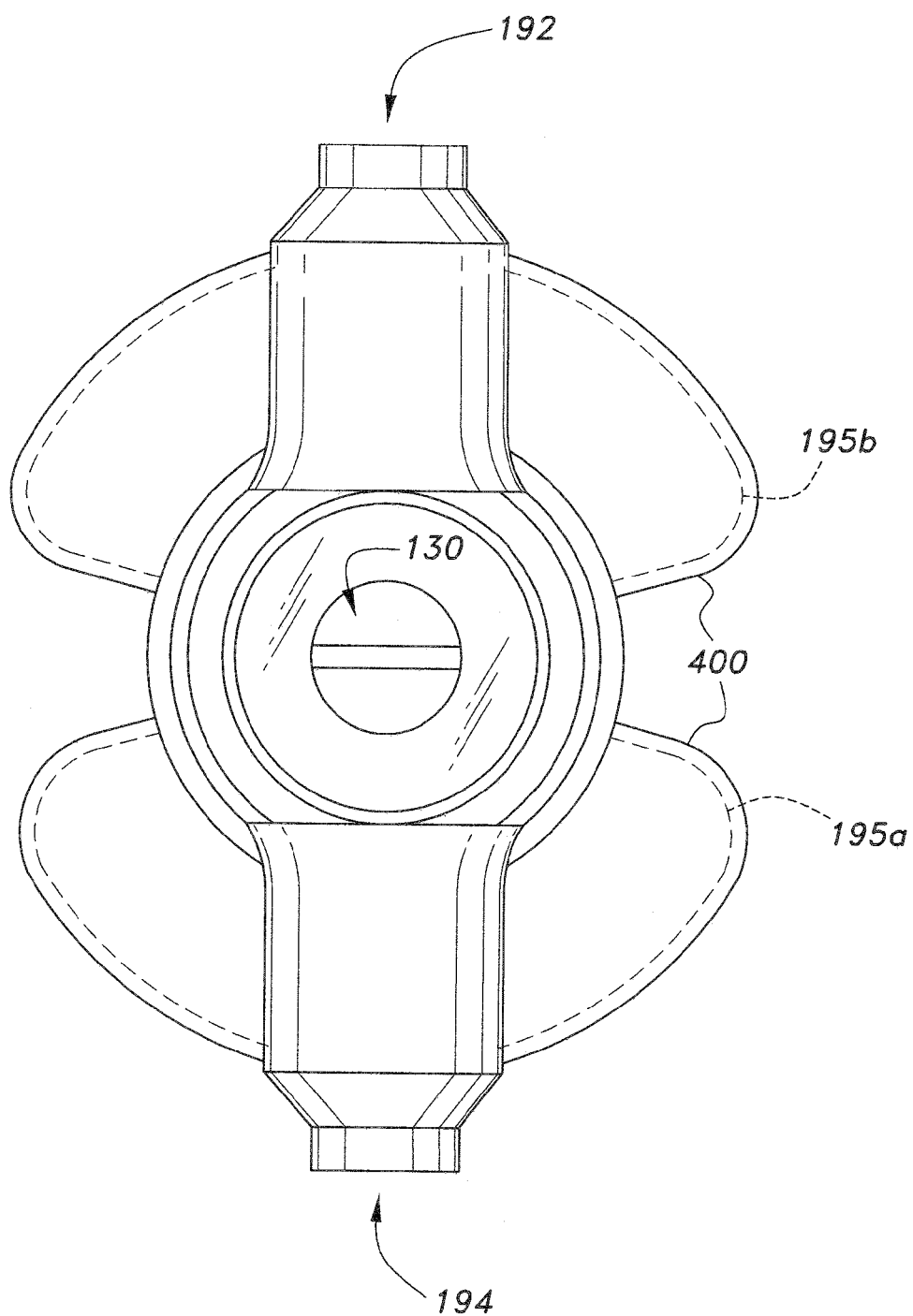
FIG. 4 is a top plan view of another embodiment of a feeding tube system including two semi-circular base plates, according to the present invention.
Figure 5:
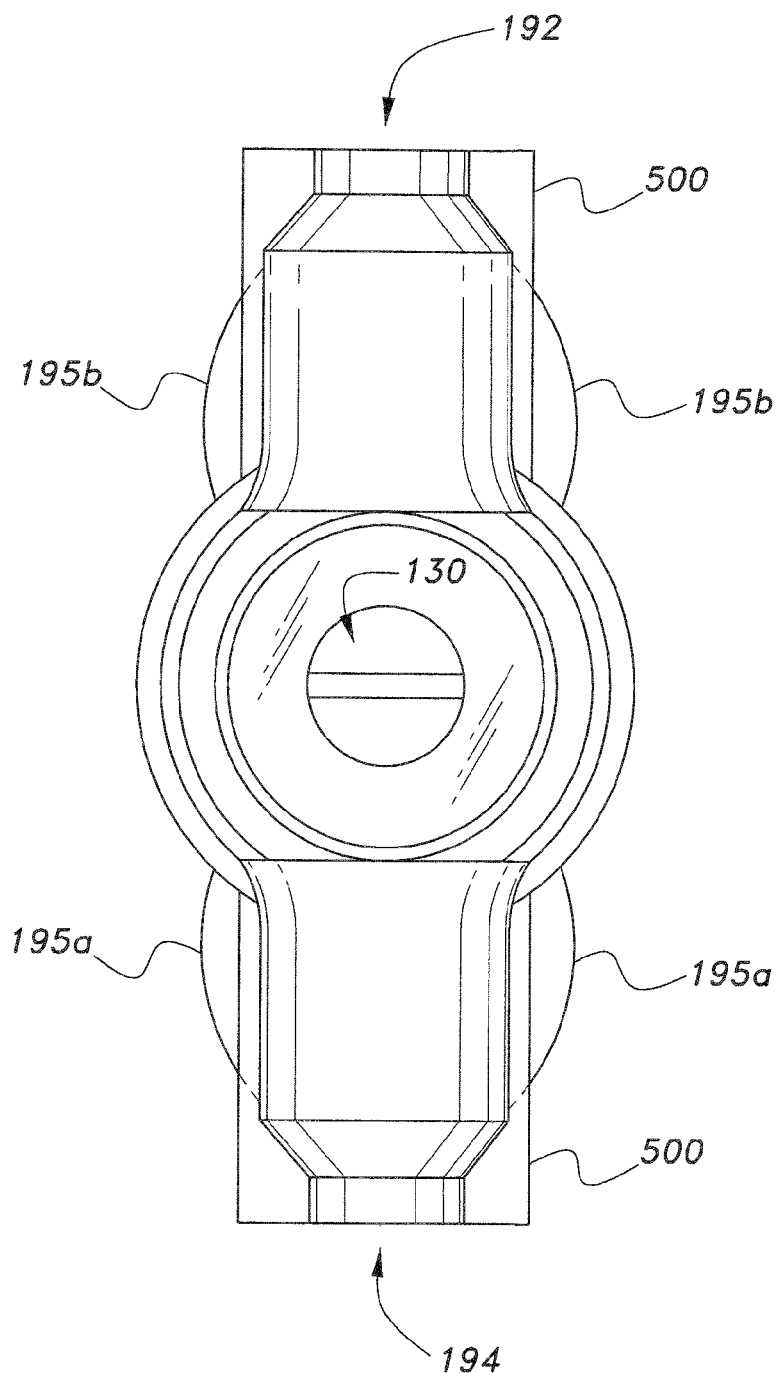
FIG. 5 is a top plan view of another embodiment of a feeding tube system including two rectangular base plates, according to the present invention.

The upper horizontal support 180 can extend parallel to the patient's abdominal wall AW. Portions of the upper horizontal support 180 and/or the lower horizontal support 185 which are closest to the shaft 110 can have a greater thickness than portions thereof which are furthest from the shaft 110. In other words, the upper horizontal support 180 and the lower horizontal support 185 can have an outer edge that is thinner than a central or inner portion thereof. The lower horizontal support 185 can be formed from a circular base plate 300, as illustrated in FIG. 3, two spaced semi-circular base plates 400, as illustrated in FIG. 4, or two spaced rectangular plates 500, as illustrated in FIG. 5. It should be understood that the lower horizontal support 185 can have other suitable shapes.

Figure 2:
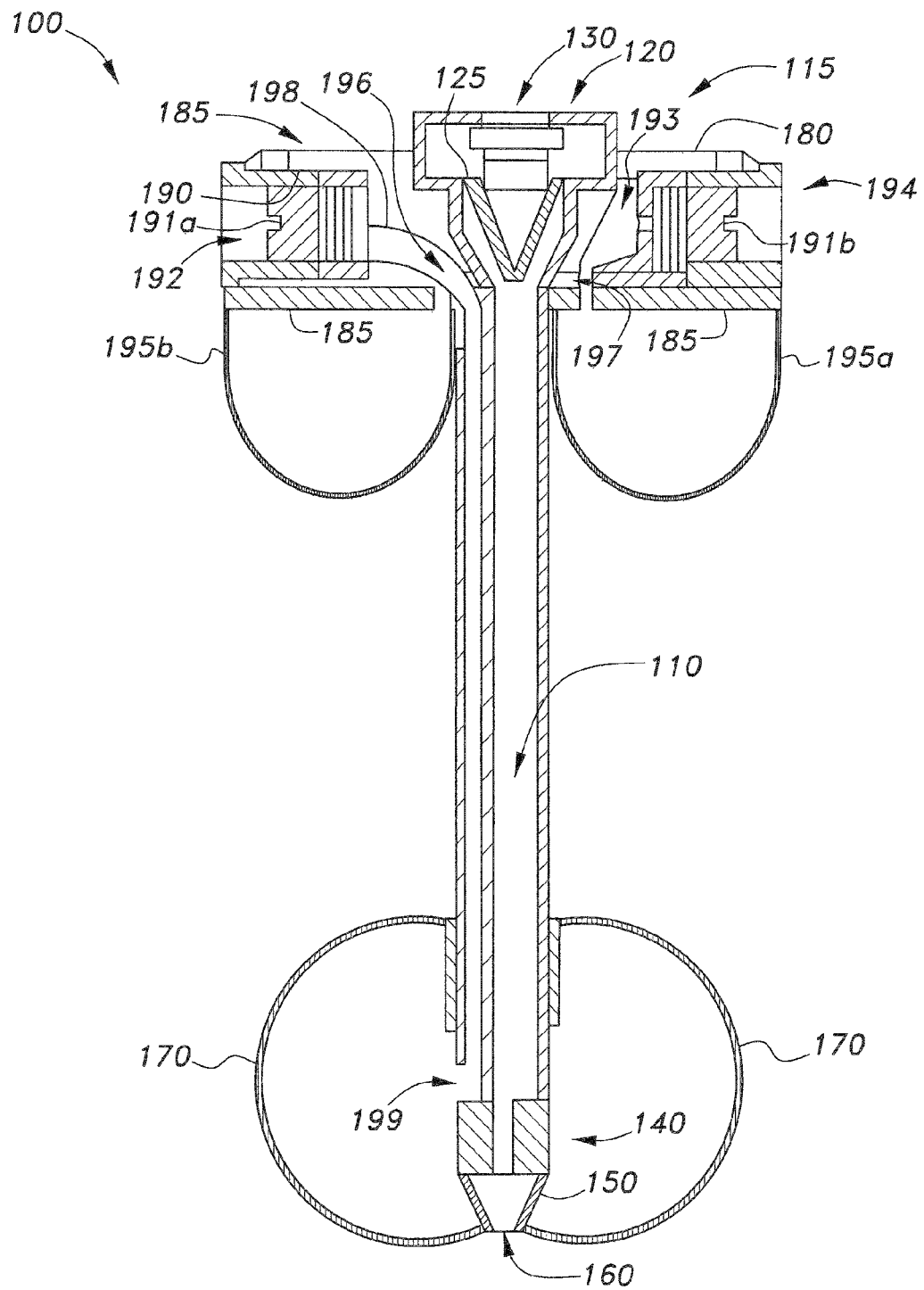
FIG. 2 is a cross sectional view of a feeding tube system, according the present invention.

The proximal portion 120 of the elongated shaft 110 can include a check valve 125, to prevent fluids from exiting the first opening 130 of the feeding tube system 100. Further, as seen in FIGS. 1 and 2, the inflation ports 192, 194 can each include a releasable one-way valve 191a, 191b, respectively, engaging wall structure 190, to facilitate inflating the balloons 170, 195a, and 195b.

The elongated shaft 110 can include a wall of uniform thickness having an outer surface and an inner surface adapted to receive fluids. The elongated shaft 110 can be formed from a flexible plastic or other suitable medical grade material, and preferably has a braided construction. Further, the elongated shaft 110 can have any length and diameter suitable to reach the patient's body cavity BC. The proximal portion 120 of the elongated shaft 110 can include distinctive indicia, such as color-coding, markings, and/or etchings to indicate orientation and depth of penetration of the elongated shaft 110 into the patient's body cavity BC.

The external base 115 can be formed from any suitable medical grade material. Preferably, the lower horizontal support 185 is made from polyurethane. Each of the balloons 170, 195a, and 195b can be formed from any suitable, strong, puncture resistant, elastic material, such as polyethylene terephthalate (PET), nylon, polyurethane, and other elastomers. The internal retention balloon 170 can be coated for lubrication or for abrasion resistance.

The external base balloons 195a, 195b can have a circular shape and a wide base for attachment to the lower horizontal support 185 of the external base 115. By way of operation, air entering into the second inflation port 194 passes through the inflation second inflation channel 193 into the first external base balloon 195a and can pass through the side channel 197 into the second external base balloon 195b. Alternatively, instead of separate first and second external base balloons 195a and 195b, a unified balloon structure 310, as illustrated in FIG. 3, can be provided, which extends across the lower horizontal portion, under the inflation ports 192, 194.

The balloon 170 can be adapted to expand to a sufficient size to secure the elongated shaft 110 in the body cavity BC and form a seal that can prevent leakage from the body cavity. The balloons 195a and 195b can be configured to expand to a size sufficient to prevent any unnecessary movement of the elongated shaft 110. Frequent movement of the elongated shaft 110 can irritate the wound or incision in the abdominal wall (AW), causing granuloma tissue formation.

Referring back to FIG. 1, it can be seen that the soft tip 150 of the distal portion 140 of the elongated shaft 110 can be inserted through an incision I in the abdominal wall AW, and into the patient's body cavity BC to thereby position the internal retention balloon 170 inside the patient's body cavity BC. Inflation of the internal retention balloon 170 secures the elongated shaft 110 within the body cavity BC and prevents the tube from slipping back out of the body cavity. Inflation of the first external base balloon 195a and/or second external base 195b lifts the external base upward, which in turn, causes the shaft 110 and the internal retention balloon 170 to be sufficiently lifted to close any gaps between the shaft 110 and the opening of the body cavity BC through which the shaft 110 extends. After the balloons 170, 195a, and 195b have been inflated so as to secure the elongate shaft 110 in place, a caregiver can administer fluids into the patient's body cavity through the first opening 130 in the proximal portion 120 of the elongated shaft 110.

It is to be understood that the present invention is not limited to the embodiments described above, but encompasses any and all embodiments within the scope of the following claims.

I claim:

1. A feeding tube system, comprising:
   an elongated shaft having a proximal portion, a distal portion, and a central lumen extending therethrough, the proximal portion including a first opening for receiving fluids and the distal portion including a soft tip having a second opening, the second opening configured for discharging the fluids into a patient's body cavity, wherein the first and second openings are aligned and continuous with the central lumen, further wherein the elongated shaft includes a check valve at the proximal portion;
   an inflatable interior retention balloon in communication with the distal portion of the elongated shaft; and
   an external base coupled to the proximal portion of the elongated shaft, the external base including:
   i) an upper horizontal support,
   ii) a lower horizontal support,
   iii) a pair of separate exterior base balloons disposed beneath and attached to the lower horizontal support, wherein each of the base balloons has a first deflated size and a second inflated size, the inflated size being larger than the deflated size, and
   iv) a first inflation port and a second inflation port, the first inflation port and the second inflation port being disposed between the upper horizontal support and the lower horizontal support and each of the inflation ports including a releasable one-way valve, wherein the first inflation port is in sole fluidic communication with the internal retention balloon and wherein the second inflation port is in sole fluidic communication with the pair of separate exterior base balloons, further wherein the base balloons are capable of being inflated to a size extending beyond the first and second inflation ports.

2. The feeding tube system according to claim 1, wherein the lower horizontal support comprises a circular base plate.

* * * * *